(12) United States Patent
Winther

(10) Patent No.: US 8,144,960 B2
(45) Date of Patent: Mar. 27, 2012

(54) METHOD FOR MEASURING THE CONCENTRATION OF A SUBSTANCE USING ADVANCED IMAGE PROCESSING TECHNIQUES

(76) Inventor: Dale E. Winther, Coarsegold, CA (US)

(*) Notice: Subject to any disclaimer, the term of this patent is extended or adjusted under 35 U.S.C. 154(b) by 765 days.

(21) Appl. No.: 12/245,523

(22) Filed: Oct. 3, 2008

(65) Prior Publication Data

US 2009/0202116 A1    Aug. 13, 2009

Related U.S. Application Data

(60) Provisional application No. 60/977,342, filed on Oct. 3, 2007.

(51) Int. Cl.
*G06K 9/00* (2006.01)
*A61B 3/14* (2006.01)
*A61B 5/00* (2006.01)

(52) U.S. Cl. .......... 382/130; 600/318; 600/319

(58) Field of Classification Search ............... 382/128, 382/130, 280; 600/319, 318, 365; 351/206, 351/221; 607/88
See application file for complete search history.

(56) References Cited

U.S. PATENT DOCUMENTS

| | | | | |
|---|---|---|---|---|
| 5,820,557 A * | 10/1998 | Hattori et al. | ......... | 600/319 |
| 6,442,410 B1 * | 8/2002 | Steffes | ......... | 600/319 |
| 6,836,337 B2 * | 12/2004 | Cornsweet | ......... | 356/517 |
| 6,895,264 B2 * | 5/2005 | Rice et al. | ......... | 600/319 |
| 7,167,736 B2 * | 1/2007 | Winther | ......... | 600/319 |
| 7,377,643 B1 * | 5/2008 | Chock et al. | ......... | 351/208 |
| 2007/0038047 A1 * | 2/2007 | Winther et al. | ......... | 600/319 |

* cited by examiner

*Primary Examiner* — William C Dowling

(57) ABSTRACT

A method and system for non-invasively measuring the concentration of an optically-active substance in a subject are provided. The system includes a light source adapted to transmit light towards a subject or object having a concentration of an optically-active substance, a polarizer positioned between the light source and the subject, an image capturing device, and a processor. The image capturing device is positioned to receive light reflected from the subject and create a measured image therefrom. The measured image defines measured light intensity data. The processor is configured to calculate a concentration of the optically-active substance based on a selected portion of the measured light intensity data.

1 Claim, 16 Drawing Sheets

1400

SIGNATURE CODE CALIBRATION TABLE

| INDEX | MGDL | PHASE C | PHASE D | PHASE E | PHASE F |
|-------|------|---------|---------|---------|---------|
| 0 | 70 | 139193 | 78208 | 70591 | 76483 |
| 1 | 80 | 67599 | 81925 | 70591 | 84015 |
| 2 | 92 | 127441 | 100782 | 44114 | 59507 |
| 3 | 105 | 116465 | 98848 | 52219 | 51448 |
| 4 | 120 | 109918 | 57084 | 51330 | 97856 |
| 5 | 131 | 102146 | 64548 | 64575 | 102456 |

HUB LOCATION MATRIX

| | | | | | | | | |
|---|---|---|---|---|---|---|---|---|
| ⋮ | ⋮ | ⋮ | ⋮ | (10,0) | ⋮ | ⋮ | ⋮ | ⋮ |
| ⋮ | ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ | ⋮ |
| (0,-10) | ⋮ | ⋮ | ⋮ | (0,0) | ⋮ | ⋮ | ⋮ | (0,10) |
| ⋮ | ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ | ⋮ |
| ⋮ | ⋮ | ⋮ | ⋮ | (-10,0) | ⋮ | ⋮ | ⋮ | ⋮ |

METHOD FOR MEASURING THE CONCENTRATION OF A SUBSTANCE USING ADVANCED IMAGE PROCESSING TECHNIQUES

CROSS-REFERENCE TO RELATED APPLICATIONS

Claim of Priority Under 35 U.S.C. §119

The present application for patent claims priority to Provisional Application No. 60/977,342, entitled "METHOD FOR MEASURING THE CONCENTRATION OF A SUBSTANCE USING ADVANCED IMAGE PROCESSING TECHNIQUES" filed Oct. 3, 2007, and assigned to the assignee hereof and hereby expressly incorporated by reference herein.

BACKGROUND

1. Field of the Invention

The present description relates to a method and system for non-invasively measuring the concentration of a substance, in particular, the concentration of glucose in a biological entity.

2. Background

In certain instances, it is necessary to measure the concentration of particular substances in a biological entity, such as a biological entity as a human. Commonly used test procedures for measuring such concentrations are invasive, requiring the drawing of blood. This can be particularly unpleasant for individuals who need to obtain concentration measurements at frequent intervals. For example, diabetic patients need to monitor the levels of glucose in their bloodstream and are required to undergo such invasive measurement procedures on a daily basis, often several times a day. Typically, the measuring is done through a finger prick to draw blood, which is placed on a test strip that is then inserted into a glucose monitoring device.

To avoid the discomfort and inconvenience of invasive testing, non-invasive methods of measuring the concentration of blood stream components of interest, such as glucose, have been developed. It is well known that the properties of glucose can rotate polarized light. In addition, changes of glucose concentration within a solution can affect the absorption of light and change the refractive index of light as it transfers to and from other optical mediums.

One location that is suitable for performing non-invasive glucose measurements is the aqueous humor of the eye. Another is the vitreous humor of the eye. The concentration of glucose in the aqueous and vitreous humor directly relate to the concentration of glucose in the bloodstream. However, the relationship between the concentration of glucose in eye fluids and its effects on light transmitted through the eye fluids is difficult to use for purposes of determining the concentration of glucose in the bloodstream. In part, this difficulty stems from the fact that accurately measuring the optical path length (l) is difficult in a structure having a geometry as complex as that of an eye. In addition, known techniques for measuring the rotation angle of plane polarized light and very small changes in the refractive index are difficult to reliably implement outside of a laboratory setting; particularly, the measurements are difficult to obtain in a setting in which such non-invasive testing will be performed by the patient or by a technician. As a result, a need has developed for a method and system that address the foregoing problems.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

According to various aspects, the subject innovation relates to systems and/or methods for measuring a change within an image of an eye comprising a cornea surface image portion and an internal eye image portion while maintaining a predetermined degree of precision in the presence of focus and imager alignment errors. The method including utilizing a surface of the cornea as a reference; and, determining the change within the image using the reference; wherein a difference between a shifted illumination gradient across the internal eye image portion and an illumination gradient across the returned corneal surface image portion is mechanically stable.

BRIEF DESCRIPTION OF THE DRAWINGS

The invention may be more readily understood by referring to the accompanying drawings in which:

FIG. 15 illustrates a structure of a signature code calibration table; and

FIG. 16 illustrates a hub centering matrix table.

DETAILED DESCRIPTION OF THE EMBODIMENTS

Figure 1:
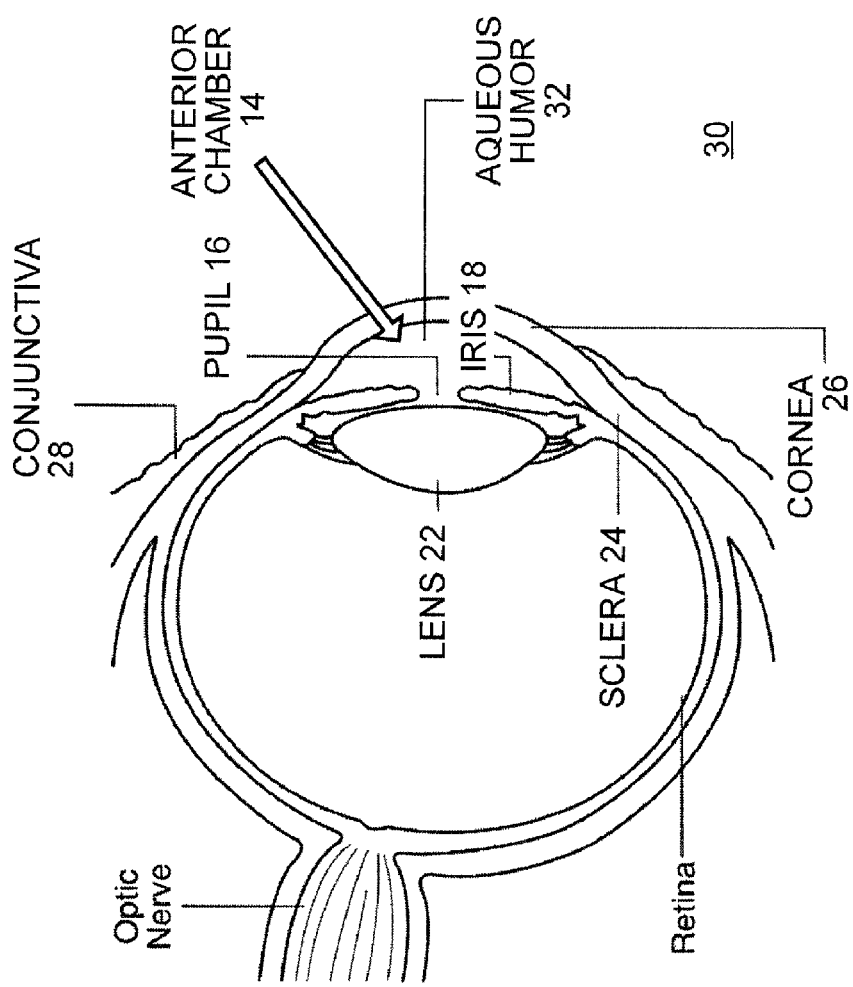
FIG. 1 is an illustration of an eye used to describe one approach for measuring the concentration of a substance in a biological entity.

The techniques described herein relate to the discovery that glucose levels in the bloodstream of a human subject can be correlated to a spatial phase shift of light that is returned from various regions of a human eye. Thus, polarized light may be passed through a glucose containing solution of the eye and the changes thereto measured to determine notably, even extremely large changes in glucose concentration produce only a relatively small degree of rotation of polarized light, absorption and changes in the refractive index when it is passed through a glucose containing solution, such as the aqueous humor or vitreous humor of a human eye. Thus, the relationship between concentration levels, polarized light rotation, absorption and refraction has proven unsatisfactory for reliably predicting glucose levels, particularly outside of the laboratory setting. However, ratios of intensities of light between the iris, retina, cornea and other structures within an eye image provides ample information to track glucose concentration changes.

Basing measurements on very small changes in light intensities is a difficult challenge. Add to this the variability of camera position orientations relative to the eye, focus and illumination instability and the challenge becomes even more difficult. The techniques described herein mitigates these issues by replacing intensity measurements with spatial phase shift measurements.

The intensity changes that occur within the light that is captured in the eye images are produced by the concentration changes in glucose content. Optical rotation, refractive index changes, absorption and other direct effects to the light impact the global intensity of the eye images returned by a camera. Changing light intensity responses that are products of refractive index changes will spatially shift the returned image. Glucose concentration changes can also produce physical changes in the eye tissues, such as swelling.

Regardless of the exact mix of intensity change and spatial shift mechanisms at work, it is possible to observe and measure correlated image shift behaviors. The measured correlated image shift behaviors track glucose concentration changes. The techniques described herein observes and tracks the internal eye image return phase-shift behaviors that accompany glucose concentration changes in humans.

Two dimensional Fourier Transforms are used to extract the spatial phase-shift behaviors of the eye image. The transformers remove the problems associated with variations in light intensities caused by camera alignment and illumination discrepancies. Unique structural features are isolated using Fourier transforms by forming spatial bandpass filters that allow the algorithm to compare the relative behavior of specific eye image components.

The global nature of the phase-shift behavior enables the algorithm to operate on very large sets of statistics. The direct result of this feature is the realization of a good signal-to-noise ratio given the inherent weakness of the basic glucose response. The massive plurality of pixels in an imaging array such as charge coupled device (ccd). Array enables the precise measurement of signals that were previously thought to be too weak to measure reliably.

The techniques described herein also utilizes global representation of the signal to compensate for significant errors in camera alignment, focus and eye orientation. This compensation affords measurement accuracy even though the subject image moves around in the frame. Which is a major concern when a human eye is imaged. Because eyes do not hold still.

FIG. 1 is an illustration of an eye 30 of a subject used in the description of the various techniques described herein. Eye 30 includes an anterior chamber 14 defined by a lens 22 and a cornea 26 that is filled with a fluid, aqueous humor 32. Eye 30 also has an iris 18 having a central aperture that defines a pupil 16. Iris 18 is surrounded by sclera 24 (i.e., the "whites" of the eye). A conjunctiva 28 covers upper and lower parts of sclera 24. Eye 30 includes a posterior chamber 54 behind lens 22, including a retina 34 that is filled with a fluid, vitreous humor 52.

Figure 2:
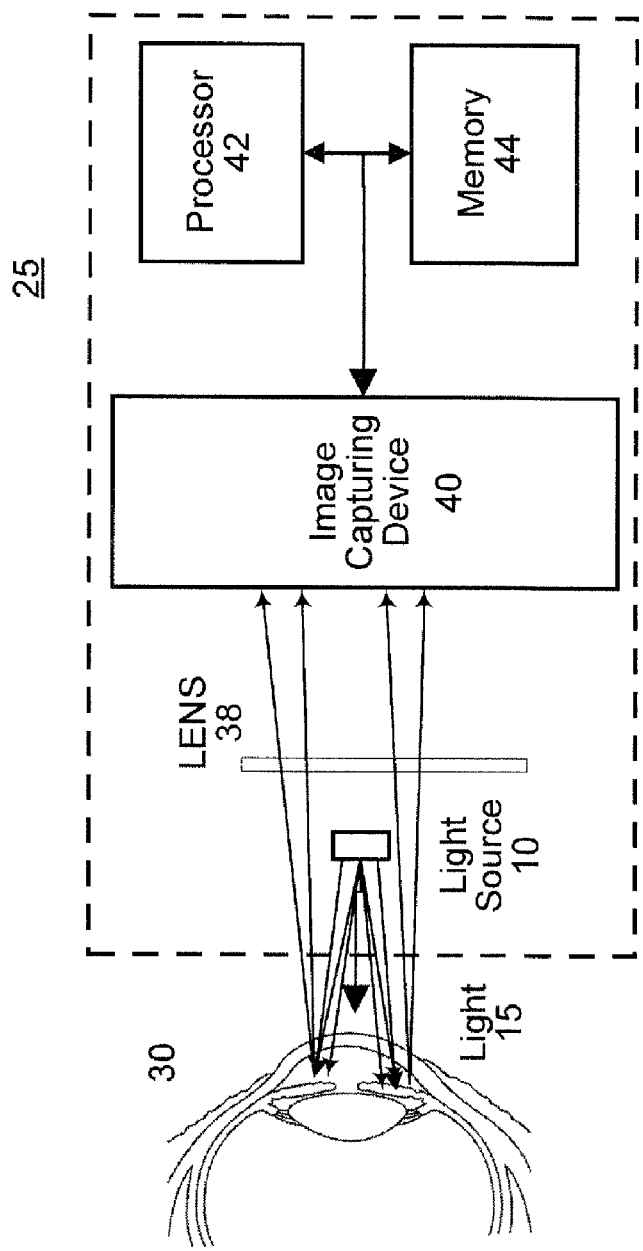
FIG. 2 is a depiction of a system for measuring the concentration of the substance.

Referring to FIG. 2, a system for measuring the concentration of a chemical substance such as glucose is provided. The system comprises a light source 10 that is adapted to transmit illumination 15 towards iris 18 of eye 30 of a subject having a concentration of the chemical substance in the bloodstream of the subject. Light source 10 is preferably placed in front of pupil 16 and is preferably a light emitting diode ("LED") or combination of LED's, each of which emits light at a different wavelength. For example, the following wavelengths may be used: 470 nm (blue), 525 nm (green), 625 nm (red), and 940 nm (near infrared). When only one wavelength is used, near infrared is preferred. When multiple wavelengths are used, blue, green, red and near infrared are preferred.

Lying in front of iris 18 in eye 30 is aqueous humor 32 that contains levels of solubilized glucose. Light source 10 provides illumination 15 to the eye 30. An image capturing device 40 is positioned to receive light reflected from eye 30. Preferably, image capturing device 40 is a ccd, such as a ccd model number CV-M50 IR manufactured by JAI Corporation of Japan, or another known image capturing device adapted to create an image from the light reflected from eye 30. A ccd has an array of light intensity detection locations called pixels. Thus, when light is received by the ccd, an array of pixels representing intensity measurements is created. The array structure of a ccd enables it to obtain an image 18 of the iris or other eye structures by measuring the intensities of light returned from it.

To increase imaging efficiency, lens 38 is preferably provided and is positioned between light source 10 and image capturing device 40 at a distance of from about 1 mm to about 5 mm from light source 10 and at a distance of from about 15 mm to about 30 mm from image capturing device 40. In an exemplary set-up, lens 38 is a 25 mm lens with an F-step of 1.4. The position of lens 38 with respect to image capturing device 40 can preferably be adjusted to improve image focus.

Preferably, the light source 10 is positioned in-line with one another and with pupil 16. Light source 10 is preferably placed at a distance of about 15 mm to about 30 mm from eye 30, with a distance of 20 mm being especially preferred. [what about lens 38? See above.]

Light source 10, image capturing device 40, processor 42 and memory 44 can optionally be provided in a unitary housing (not shown), and more preferably, in the form of a portable, hand-held unit. The components of system 25 can also be separately connected without the use of a unitary housing. Also, two or more of the components can be combined in a single housing and then separately connected to or used with the remaining components.

According to the configuration of the exemplary system depicted in FIG. 2, light source 10 is positioned such that the light strikes the iris 18 of eye 30. A portion of the light strikes iris 18 and returns towards image capturing device 40. The passage of the light through the aqueous solution imparts a spatial displacement to the image. The phase-shift in the return image provides data that allows the detection of the amount of glucose within the eye 30.

As a result of the foregoing, it is theorized that the spatial phase shift in the intensities of light that are returned from the iris image can be used as an indirect measure of glucose contained within the anterior portion of the eye.

Construction of a Signature Code Match Table

Returning to of FIG. 2, memory 44 of system 25 that is operatively coupled to processor 42 and contains both predetermined glucose concentration data and predetermined image spatial phase shift data. Memory 44 preferably includes a signature code match table of predetermined spatial phase shift data versus known concentrations of glucose.

In one approach, a signature code match table is generated for each subject, to be used to predict the glucose concentration of that subject.

Figure 4:
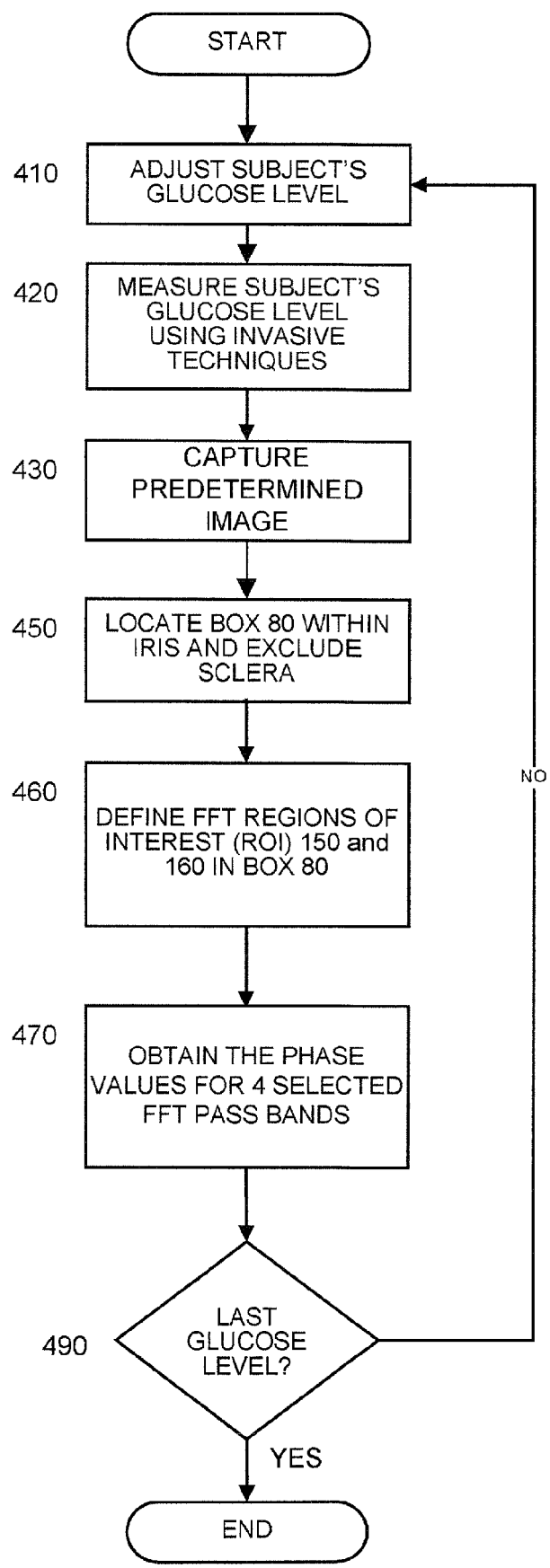
FIG. 4 is a flow chart depicting a method for generating predetermined light intensity data and predetermined concentration data performed in one exemplary fashion.

FIG. 4 is a flow chart depicting some approach for generating a signature code match table. In step 410, glucose is supplied to the subject to adjust the subject's glucose concentration. The glucose can be supplied, for example, by having the subject ingest glucola of fruit juice. After waiting for a period of time, preferably ten minutes, for the glucose to enter the bloodstream, the concentration of glucose in the subject's bloodstream is measured in step 420 using known invasive glucose measurement techniques.

Once the known concentration is established, light from light source 10 is directed towards eye 30 through a polarizer (which may be optional). In step 430, light reflected from eye 30 is received by image capturing device 40, and one or more images are captured. Images generated as part of creating the signature code match table will be referred to herein as "predetermined images" to distinguish them from those images that are generated for the purpose of measuring an unknown concentration of glucose or other chemical substances. Images obtained at unknown concentrations will be referred to herein as "measured images."

In step 430, light source 10 and image capturing device 40 are preferably positioned such that a certain amount of light which strikes the iris of eye 30 scatters light back as an image containing intensity values that are subsequently detected by image capturing device 40. Light returns from the iris are affected by refractive index changes that are caused by the transitions between optical mediums in the image path. Light source 10 is placed at a distance of from about 15 mm to about 30 mm from eye 30, with a distance of 20 mm being especially preferred. Light source 10 is preferably placed in front of pupil 16. Lens 38 is preferably positioned in-line with light source 10 and pupil 16 at a distance of from about 1 mm to about 5 mm from light source 10. Image capturing device 40 is preferably positioned in-line with light source 10, lens 38 and pupil 16 at a distance of from about 15 mm to about 30 mm from lens 38.

Image capturing device 40 captures an image of the iris of eye 30 by measuring the intensities of light received at the various intensity measuring locations in the device, such as at the pixel locations in the image sensor (e.g., ccd) of the image capturing device 40. As a result, an image of the iris 18 is created. The image comprises the of intensity measurements generated by the image capturing device 40. Preferably, the image is generated using a single wavelength of light 15. If multiple wavelengths of light are used, as will be described later, they are preferably used to generate a series of different images, each based on a single wavelength.

FFT Processing

A very small optical shift event can be observed in the human eye when blood sugar levels are changed. Changes in the intensity and relative orientation of images that are behind the cornea can be observed. The effect is Global. Different camera angles and fields of view portray the same event.

The eye image consists of scenery information that produces a picture of, for example, the iris 18. When a light source 10 like an LED is returned (reflected or scattered) from the iris 18 an illumination intensity gradient is produced across the image. The gradient spreads out in a circle from the central bright spot of the beam.

Scenery information can be seen to modulate the return of the illumination gradient. The image contains high frequency scenery data and low frequency intensity gradient data. The frequencies discussed here are Spatial Frequencies. Periodic behaviors relative to space instead of time are considered. For example, a group of pixels that become 20% brighter and then 20% dimmer and repeat every millimeter across the image surface has a specific spatial frequency. F=1 cycle per millimeter.

The FFT processing transforms spatial behaviors into the frequency domain. Images contain spatial behaviors in the images that plot on the X and Y axis simultaneously. A two dimensional Fourier Transform is used to process images.

When an image is put into the frequency domain it is easy to separate the frequency components with filtering techniques. A high-pass filter will reveal the iris scenery data and a low-pass filter will reveal the illumination gradient. The low frequency gradient data provides a global image response to the sugar-induced phase shift event.

At any point in the global view, the illumination gradient in the returned image shifts with a change in sugar concentration. The gradient position within a given region of interest (ROI) changes relative to the centroid of the illumination.

The intensity changes in the image can be seen within any ROI. However, because the intensity changes are very small, it is difficult to get a reliable measurement. Small changes in illumination brightness or positioning errors of the image capturing device 40 preclude making reproducible measurements. Although direct intensity measurements can be made, it is not practical to do so with human eye subjects.

Evaluating the shift of the intensity gradient is much more reliable. The key to success for doing this is to have an accurate shift reference point. One method is to compare the shifted position to the absolute center of the illumination bright spot. The technical obstacle for doing this is that a large number of pixels in the center spot are often right at intensity saturation when the image is viewable. The exact center pixel cannot readily be located. Furthermore, for a given shift event the change is often less than one pixel in distance which precludes an exact distance measurement.

The good thing about the spatial gradient shift is that it involves all of the image pixels. Even a small global shift will cause hundred or thousands of pixels to receive a change in intensity. What is not known is which pixels will change for a given shift. The application of statistical tools to the image will detect the apparent gradient shift.

The resolution to the precise reference problem can be made by comparing a shifted image with an un-shifted image. Consider that the LED illumination causes light returns from the corneal surfaces. These returns are un-shifted. The image capturing device 40 receives light from the iris image and also from the corneal surface images at the same time.

The FFT process can calculate very small phase changes that take place when the combined iris and corneal surface images are evaluated. A ROI consisting of 100×100 pixels provides 10,000 pixel measurement pairs that can statistically resolve very small image shift events. It is easy to see that if the ROI is moved to another location over the image that similar comparisons can be made between the iris gradient and the cornea gradient for each unique position.

Since the illumination gradient is a continuum for both images, moving to another ROI still produces the same result. This process greatly reduces the need for precise camera to eye orientation precision. The internal spatial relationship between the two eye images provides the measurement.

The surface reflection contains cornea curvature properties that must be considered when it is used as a measurement reference. When viewed as a separate image, the cornea will induce an intensity gradient track that encodes its radius. To use this image as a monotonic shift ruler it is necessary to tune the process to the radius of the cornea 26.

Selecting the appropriate spatial pass-band with a low-pass FFT filter can produce a monotonic index. This index "flattens" the curved ruler into a nearly linear spatial reference for the background (iris) image. The iris and cornea images can be directly compared for relative spatial phase shift changes.

When a passband is tuned to the corneal radius, the majority of the pixels in a phase measurement will agree. In other words, most of the pixel phase values for the ROI (just the cornea 26) will be the same. The standard deviation for the individual phase measurements within the ROI will be near unity. If some portion of the image diverges from the tuned radius, the standard deviation of these pixels will change.

The tuned cornea passband is fairly low in frequency. That means that when this pass-band is applied to the iris image the high frequency scenery data will be filtered out. The FFT will measure the phase differences between the two images. The farther the iris gradient image shifts, the larger the change in the standard deviation is for the phase measurement pixels within the ROI. In other words, the tuned phase measurement pixel standard deviation will produce a monotonic track of the global image shift behavior. At this point the sugar concentration can be directly read as a unique standard deviation value.

Figure 7:
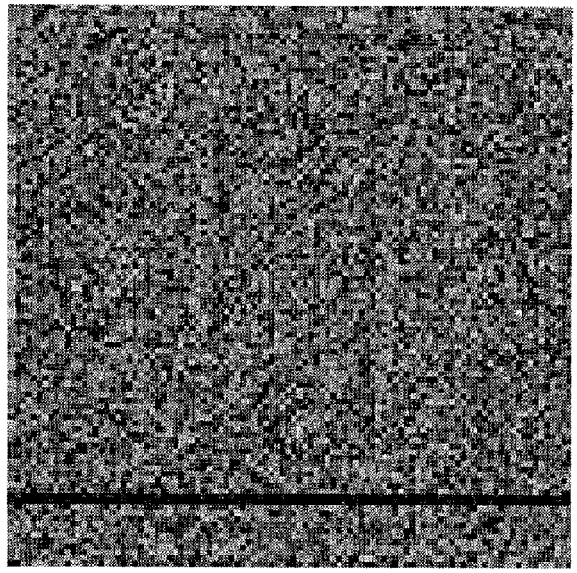
FIG. 7 illustrates an exemplary Fast Fourier Transform (FFT) phase image and the placement of a narrowband integration column.
Figure 8:
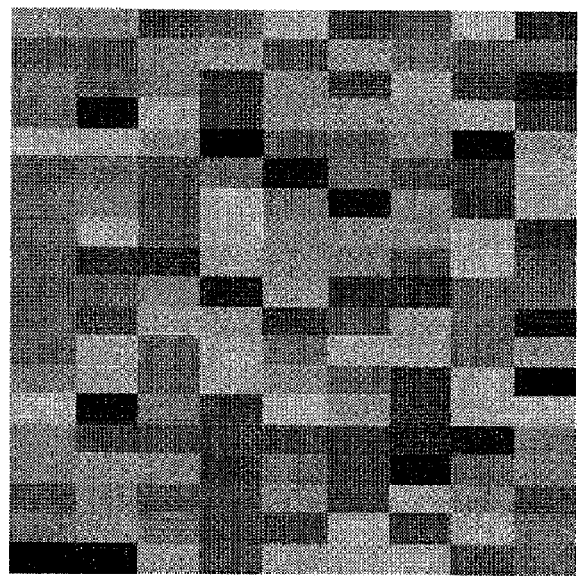
FIG. 8 illustrates a magnification of a small section of the phase image of FIG. 7.
Figure 9:
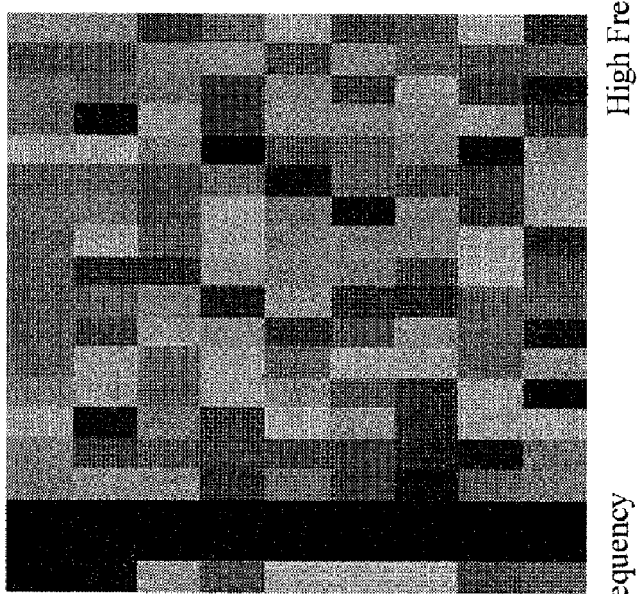
FIG. 9 illustrates the phase image magnification with a 2-column passband over it.

FIGS. 7-9 shows how the tuned phase data is recovered from the FFT phase image. The phase image is ordered such that the left side of the image contains low frequency data and the right side of the image contains high frequency data.

Placing an integration column over the appropriate pixel columns selects a specific passband. The width of the column determines the bandwidth. The pixels underneath the integration column are quantified to track the image shift event. This is accomplished by calculating the standard deviation of the pixels under the integration column.

When the integration column is placed and tuned (width set) correctly, the returned image affects the phase response under the column and the standard deviation of the column is used to quantify the phase shift. A 100 high by n pixel wide column incorporates the global optical shift event for the entire 100×100 pixel region of interest. Statistical concurrence of the phase shift is thus measured for the entire processing box. 10,000 pixels are used to determine the concentration.

The standard deviation of the integration column portrays the global phase shift of the underlying image within the ROI. A low standard deviation implies passband synchronization with a specific phase value. A large number of pixels agree with the column phase value. A high standard deviation implies that a large number of pixels disagree with the column phase value.

As the image becomes increasingly phase shifted, the passband column standard deviation tracks the phase shift continuum. Since the passband is tuned to the corneal radius, a monotonic shift event index is produced. This index is used to measure blood sugar concentration.

FIG. 7 shows the actual FFT phase image and the placement of a narrowband integration column.

FIG. 8 shows a magnification of a small section of the phase image. The pixels are enlarged to show the behavior. The gray shades of the pixels encode phase data for image content at specific spatial frequencies.

FIG. 9 shows the phase image magnification with a 2 column passband over them. The standard deviation of the pixels under the integration column quantifies glucose concentration by tracking the spatial phase shift.

Figure 10:
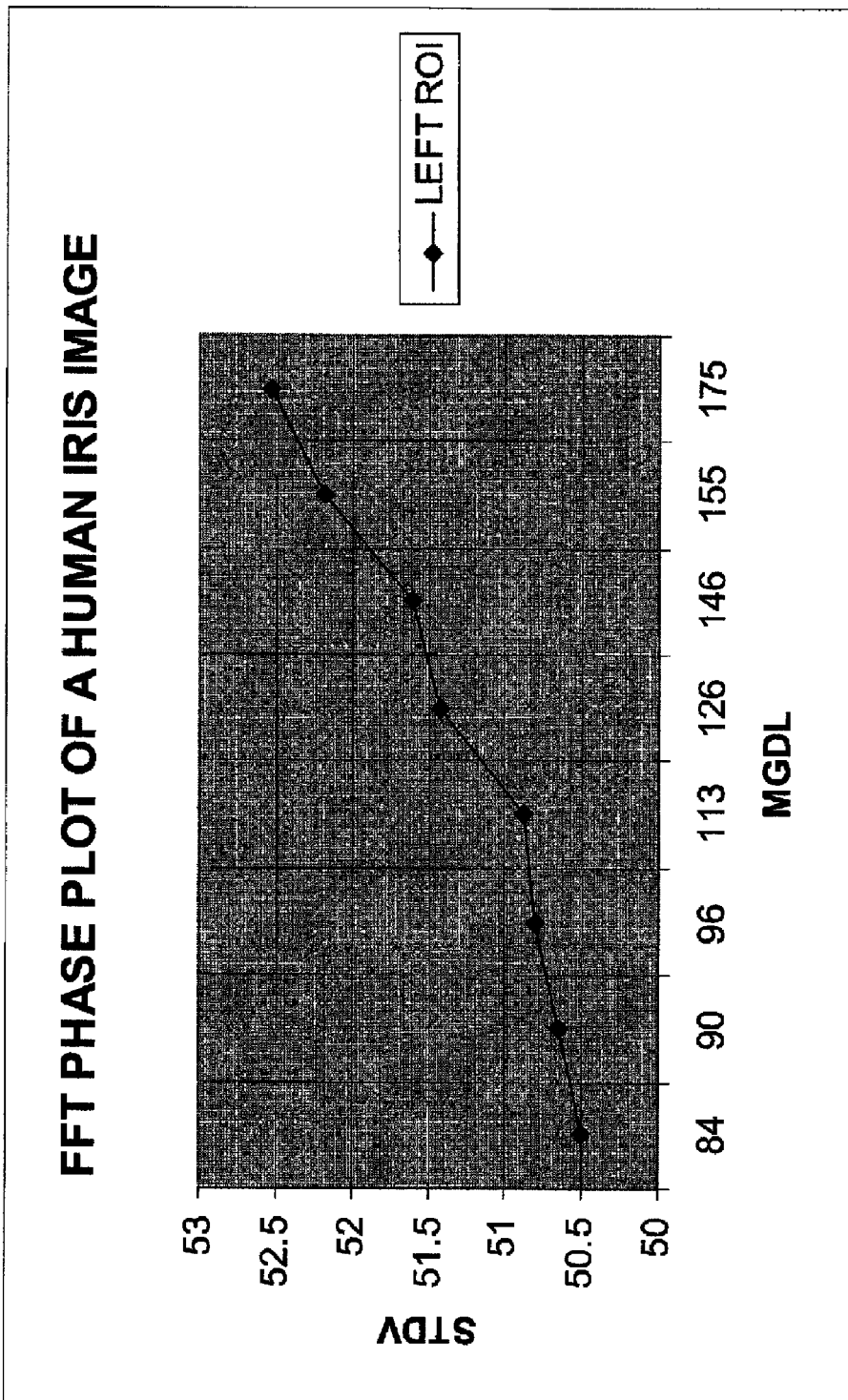
FIG. 10 illustrates an integration column standard deviation plot for an iris image.
Figure 11:
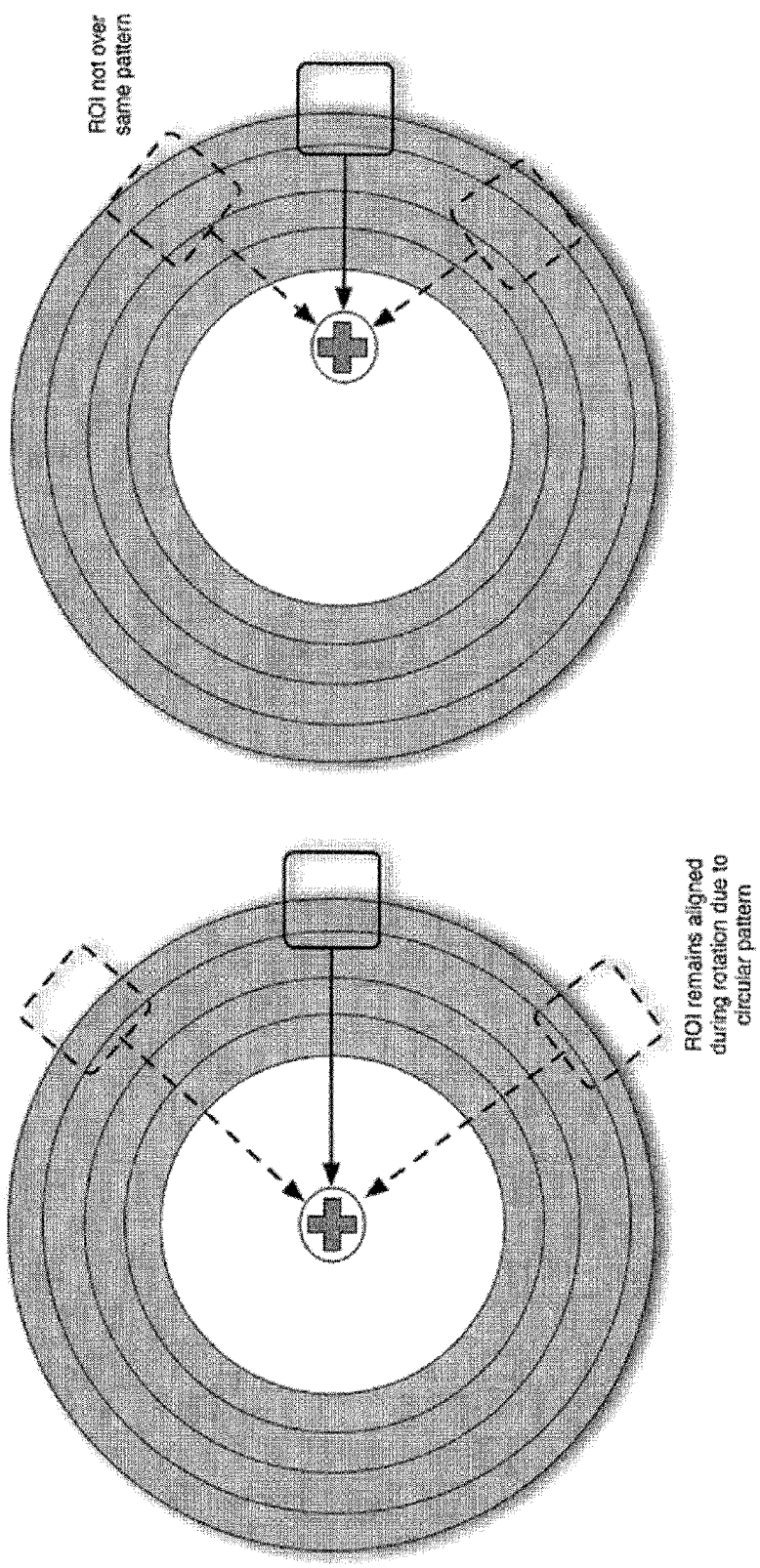
FIG. 11 illustrates a comparison of the alignment of image rotation hubs of FIGS. 12 and 13.

FIG. 10 shows an integration column standard deviation plot for an actual human iris image return.

The plot is a direct phase measurement of the image without any compensation for orientation precision or parametric offsets. It is therefore not truly linear but demonstrates the actual, unprocessed monotonic glucose tracking response.

FFT Multi-Band Phase Coding

Tracking the glucose induced shift in the eye requires a high degree of measurement certainty. The use of a single FFT passband can yield a monotonic track when all orientation and alignment issues are satisfied. Precision image capture alignments are difficult to achieve. When the images are not perfect it becomes necessary to compensate for small orientation errors.

Because the eye image returns to the camera through a convex aperture, the pathlengths through the fluid cavities are different for each pixel of the detector. A graduated change in image amplitude and spatial displacement is produced by the shift event. This behavior produces unique responses within different spatial passbands.

The cornea presents two distinct radii. The average external radius is about 7.8 mm and the internal radius is about 6.55 mm. A narrow spatial passband is tuned to the external radius and yields a monotonic track of the shift event.

Additional passbands can be used simultaneously to follow the shift. The internal corneal radius and other spatial frequency components within the image can be used as tracking confirmation. From a common image vantage point, the relationships between each of the passbands are mathematically linked.

The linked relationships between passbands provide for a significant tolerance to camera position and alignment errors. The observation of the eye image from skewed camera angles can produce a reliable measurement where eye geometry is consistent. An image swath that corresponds with a constant curvature rate can be used to statistically validate shift measurements.

Changes in surface and interior spatial relationships take place between the FFT reference image (corneal surface return) and the interior image. Precise focal distances between the camera and the eye have a minimal effect on this relationship. As a result, the measurement is highly immune to minor image capture focusing errors.

The tracking waveform is unique for different passbands. Correlating the waveforms of several passbands as a function of the shift event produces confirmation of a specific glucose concentration. This is called a glucose concentration signature code. These codes can be compared with similar concentration codes within a fixed calibration table.

An illumination gradient radiates laterally from the light source spot beam centroid. The FFT is used to track the gradient differences between the corneal surface image and image data that is returned from the interior eye surfaces. Interior images can be acquired from the Iris, Retina, Lens surface or any tissue that scatters light.

The FFT follows the spatial phase shift between a reference image and the shifted image return across the two dimensional image at the detector array. Inconsistent scenery modulated pixels can disrupt the gradient comparison process. A low pass filter that is tuned to correspond with the corneal radius removes eye feature detail. A monotonic translation of the shift event relative to the corneal curvature is made possible.

The primary function of the low pass filer is to tune the tracking process to the eye curvature. Multiple shift responses are tracked to add statistical validation to a measurement. Tuning the two corneal surfaces relative to the internal image returns provides the primary means of measurement. Additional image properties provide useful processing information.

Spatial passbands that are not tuned to either curvature also provide useful shift data. They are correlated with the monotonically tuned passband responses within a look-up table. In addition, it is also useful to track higher frequency scenery clusters that show the shift event.

Scenery clusters can be directly correlated by choosing a harmonically related passband. The curvature tuning remains while clusters of higher frequency shifted scenery data appear within the same passband. This results in an overlay passband that can also produce a monotonic shift plot.

If the human eye could be held perfectly still the ability to directly compare the signature code phase shift values between an unknown concentration image and a calibration image would be quite simple. Unfortunately, eyes do not hold still.

The Real-time image capture process can only come close to precision orientation repeatability. A method has been devised to increase the correlation precision between the unknown and calibration images. The absolute position of an unknown concentration image relative to a similar image previously stored in a calibration table can be dynamically located. This process permits accurate concentration measurements to be made even though significant image orientation discrepancies exist.

During calibration, images are captured and stored when the subject's blood sugar is at different concentration levels. The signature codes are extracted from the images and stored in sequential concentration order. This produces the calibration table.

The task of assuring that the signature code components of an unknown image truly match the relative values of a concentration code in the calibration table is accomplished by the orientation engine. There are 4 major components to the engine. They are:
  1. Compare code elements to all calibration table entries
  2. Rotate the global image through the FFT processing box
  3. Adjust the image's X and Y position to find the common rotary hub
  4. Acquire statistics during image rotation to confirm global consistency.

These steps are repeated until the best concentration comparison is located.

The algorithm theory is based on the fact that when an unknown image has the same rotation hub as a known calibration image the concurrence of correlation between the signature code components are valid. It is a technique that confirms the unknown image orientation with a known concentration image.

In other words, when the rotary hub of an unknown image matches that of a known image the relative tracking values between the signature code components express a valid mathematical relationship for the concentration. The signature code components of the unknown and known concentration images are in geometric alignment.

When geometric alignment is achieved the relationships between the reference (surface image) and the measured image (passed through solution) are retained. This allows for observations of the image at different camera alignments and distances. These are common issues when viewing an eye. The problems associated with varying camera positions and focus is mitigated.

The current system uses a signature code that is comprised of four spatial passband phases. They are calibrated to the individual subject. A least one passband should be tuned to produce a monotonic glucose track. This is the primary tracker.

Three additional passbands are chosen to yield unique tracking patterns. Bandwidths are adjusted to exhibit unique tracking behavior. Passbands are set to demonstrate unique phase relationships between the code components.

The four passbands are evaluated during each comparison step to determine if a plurality of passbands agrees with the same estimation of concentration. Multiple passband table comparisons must agree or nearly agree on a match. In addition, one of the passbands in agreement must contain the primary tracker.

Multiple passband agreement includes the interpolation process that produces concentration value estimations that lie between fixed table entries. The process of determining that multiple passbands agree functions by selecting the concentration value that is nearest the value found by the primary tracker. If an additional passband has its best fit within plus or minus one calibration table entry it is considered to be a confirmation. The average of the concentration values that were obtained by the each of the confirming passbands is used as the estimation value.

Statistical behaviors are used to confirm global viability and to locate the image rotation hub. The unknown image is rotated through the FFT processing ROI box from −11 degrees through +11 degrees. A four passband comparison is made every 0.1 degrees of image rotation. When the unknown image rotation hub is the same as the known image hub a track is produced with a reduced point-to-point standard deviation. The rotational point where the primary tracking passband locates the smallest delta against a stored value in the calibration table is evaluated.

Figure 12:
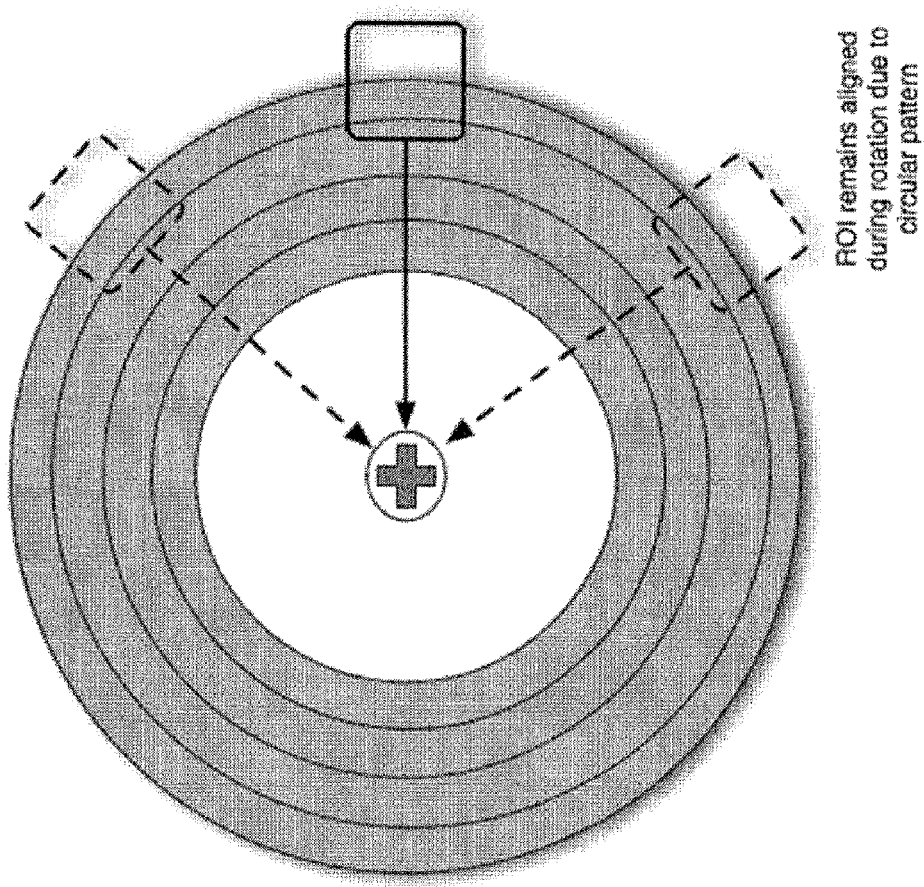
FIG. 12 illustrates a properly aligned image rotation hub.

FIG. 12 portrays the statistical acquisition of a properly aligned image. Successive gradient samples are compared as the computer software rotates the image through the FFT processing box. When the rotation hub is precisely aligned, all of the comparisons take place at the same radius from the centroid. Global statistics are collected by making repeated measurements of the illumination gradient differential phase shift.

Figure 13:
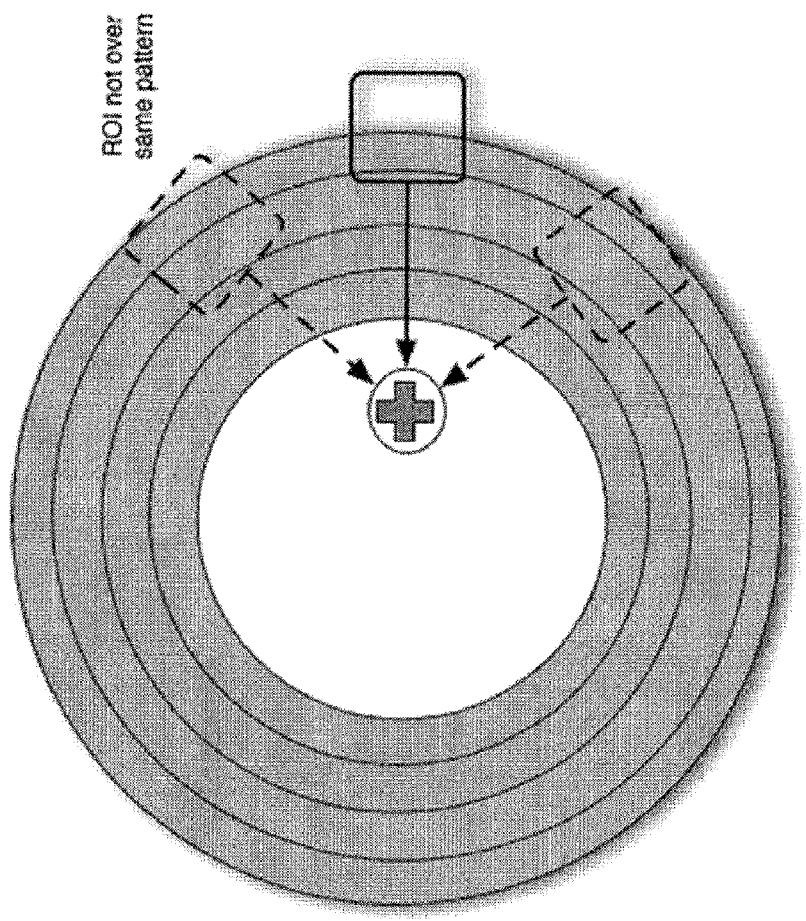
FIG. 13 illustrates an improperly aligned image rotation hub.

FIG. 13 shows what happens when the rotation hub is not centered. The image rotation exhibits a wobble that can be visualized by observing the circular line as it passes through the FFT processing box. Each spatial gradient measurement is made from a different centroid to sample radius point. Consistent statistics can not be obtained.

Ideally, multiple passbands should agree such that each one shows the smallest phase delta at the same rotational position. When this is true the rotary search process has identified a case where all best comparisons are synchronized. A synchronization ratio (SRATIO) value of 1.0 exists. Due to tracking noise from scenery pixels the SRATIO may not be observed at a perfect 1.0. Each passband comparison locates its best comparison delta independently. A substantial candidate for a glucose concentration match is located when the SRATIO is closest to one.

The hub location is found through an iterative search process. The X and Y axis of the unknown image is shifted on a trail basis prior to the rotary hub search operation. An X and Y shift step matrix is produced. The image X axis is shifted from, for example, −10 to +10 pixels. The Y axis is also shifted over the same range. A grid square orientation sequence is executed with each new position going through the signature comparison and image rotation process. This is performed while looking at each node in the calibration table.

Ideally, only one set of signature codes will match between the unknown and calibration data sets. It is possible that more than one match will be indicated when the signature code comparisons are numerically close. Supplementary measurements are used to assure that correct choice has been made. Evaluation of the additional statistical parameters ultimately identifies the best answer.

The three best measurements (relative to the best primary passband phase delta) are used for a more detailed analysis. Parametric voting is used to make the final choice. The statistical elements for the consideration are:
BDSUM (Best Delta Sum)
DSUM (Delta Sum)
QV (Q Value)
PTQV (Primary Tracker QV)
ADEV (Array Deviation)
SRATIO (Synchronization Ratio)
AGREE (Number of passbands in agreement)
CPDR (Cluster Proximity Deviation Ratio)

The BDSUM value finds the best comparison between the Primary Tracker/best support passbands and an entry within the calibration table during the rotary scan and image axis step search. BDSUM is the average of the best multi-band comparison deltas at the rotary position indexed by the Primary Tracker. The three lowest delta points are used to identify the candidates for further processing.

DSUM is the average of the best comparison deltas for all of the contributing passbands regardless of their rotary position orientation. It provides a measure of the comparison quality of the selected passbands irrespective of orientation synchronization.

The most likely answer will usually associate with the rotary location that exhibits the lowest average ADEV for the group of passbands that agree with the same concentration estimation. It measures the combined passband quality of tracking smoothness during the rotary scan process. With a good hub alignment the step-by-step deltas between the known calibration data and the unknown image should yield a low standard deviation.

QV is a parameter that measures the sharpness of the best fit response during the rotation process. It counts the number of times that a specific concentration is estimated using each of the passbands that are in agreement. A large QV indicates a high probability that the selection is correct. As the rotary scan takes place the maximum number of positions that agree with the same answer implies a probable choice.

PTQV is a QV measurement using only the primary tracker. It factors into the voting process as a Q confirmation of the most monotonic passband match during rotation.

SRATIO confirms the closeness in rotary position orientation between the passbands that agree on a specific concentration. It indicates how well the passband matches are synchronized in rotary space.

AGREE gives further weight to the decision by indicating how many passbands agree with the same answer. A higher passband agreement count along with validating statistics argues for the best estimation.

CPDR (Cluster Proximity Deviation Ratio) forms a three element cluster of the best passband deltas for a given estimation. CPDR is used to measure how close the specific deltas are between the passbands and the specified the answer. It is a ratio between the highest and lowest delta in the matching set. A high CPDR value usually indicates that an irrational comparison has been made. All of the passbands should have table comparison deltas of similar magnitude.

Parametric Boundary Limits are used to invalidate statistically derived estimations that may be unreasonable. A method of detecting the violation of sanity thresholds has been incorporated. The response to one or more boundary limit excursions is the production of an error indication. Error indications can be used to determine that a measurement was invalid due to optical artifacts, such as eyelids or skin in the image. It can also be used to detect concentrations that go beyond the calibration range of the individual.

Often, boundary limits can be exceeded by the detection of conflicting statistical results. A number of imaging issues can produce this response. Such events as large and or spatially inconsistent orientation and focus situations can cause the error.

The most basic response is the issuance of an error message that requires a new image to be taken. Alternatively, the system will automatically process another image that was taken during the image capture process. Multiple sub-frames are captured during each eye measurement that allow for automatic error recovery. The entire algorithm is repeated for the additional frames until an image is processed that exhibits reasonable statistical relationships.

Use of Multiple Light Wavelengths

The technique that has been implemented in the above example operates with a monochrome CCD camera. Other image array detectors and color imagers can be used as well. Two alternative implementations that utilize the fundamental components of the algorithm are envisioned. Multiple light wavelengths in the visible and/or near infrared can be applied to the further enhance the precision and repeatability of glucose measurements.

Method one would replace the supplementary spatial passbands from a monochromatic image with spatial passbands that are acquired from multiple wavelength images. A color camera, for example, would supply three images for processing. Each image presents a unique shift rate to the algorithm that can be tuned and tracked.

Method two would perform the original monochromatic multiple spatial passband processing on each color independently. The final results from each color's glucose measurement would be compared for agreement to confirm the reading.

FFT Signal Extraction from Regions of Interest (ROI)

In step 450 of FIG. 4, a data set represented by box 80 (FIG. 3) is selected to include iris image 70 but exclude sclera image 60. In a preferred embodiment, sclera image 60 is excluded from the captured image by pre-setting the field of view of image capturing device 40 to a diameter that is less than or equal to an iris diameter that is typical for most subjects. However, other techniques such as threshold detection can be used to determine the location of sclera image 60 and exclude it from box 80.

Figure 3:
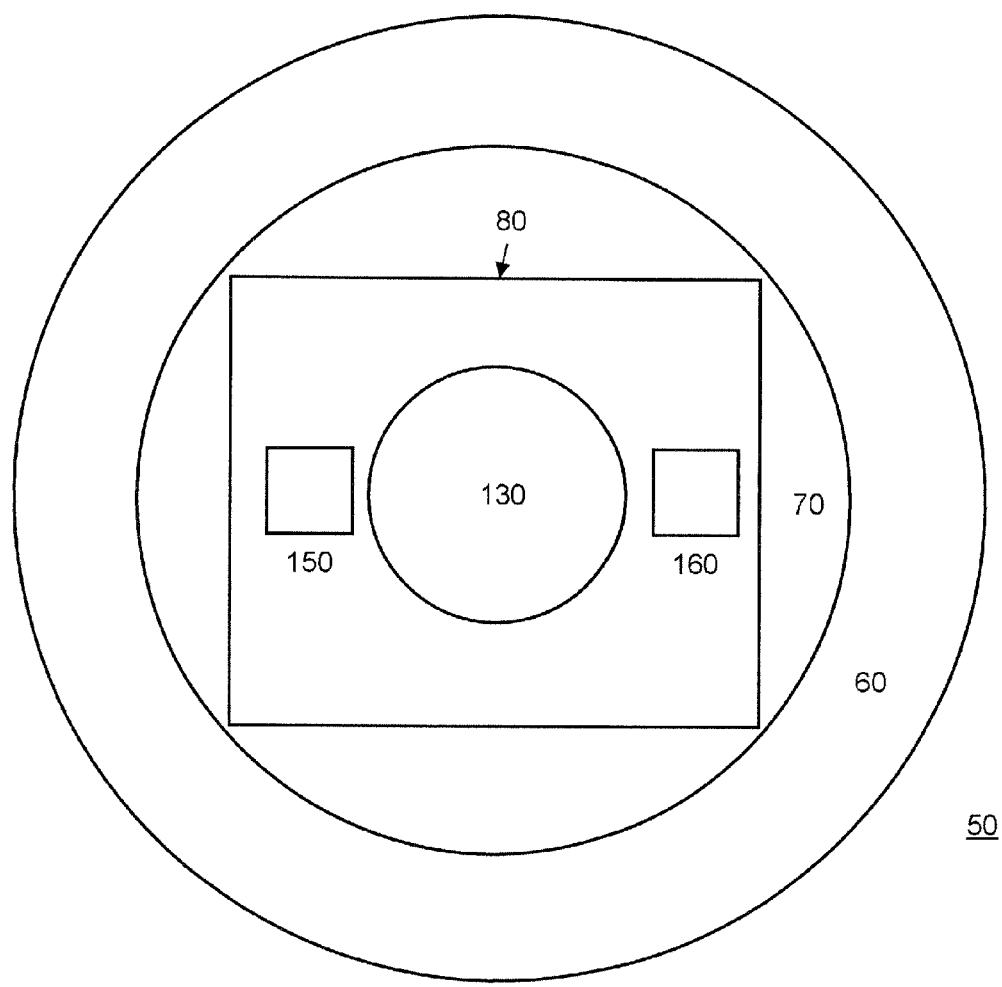
FIG. 3 is a depiction of an image of an iris of the eye of FIG. 1.

According to step 460, a pair of FFT regions of interest (ROI) 150 and 160 is defined in iris image 70, each of which corresponds to a particular region of the iris. As shown in FIG. 3, FFT ROI 150 comprises a rectangular region 155. FFT ROI 160 similarly comprises a rectangular region 165. These regions are preferably square in nature and are positioned with respect to one another to create calculation spaces in different areas of iris image 70. In another preferred embodiment, these regions may be of other shapes. In one preferred embodiment, a region of interest, such as a 100 pixel×100 pixel box over a portion of the eye image, FFT phase processing can resolve the glucose induced spatial changes in the image. Furthermore, sequential processing of more than one processing box can be used to valid results or arbitrate a vague answer.

Pupil 130 lies within iris 70, and thus, the image of the iris includes the pupil. However, the pupil is not used to calculate the concentration of the chemical substance and does not lie within the FFT ROI 150 and 160. To measure the glucose induced optical changes, the FFT is used to process spatial phase changes. The FFT provides immunity to intensity variations and many orientation discrepancies. Use of the ROI spaces permits measuring on the image center line, which avoids eyelid interference problems.

As explained earlier, the present invention relates to the discovery that ratios of intensities of light returned from a subject can be used to predict glucose concentrations. It has also been found that light intensity measurements can be subject to "pitch and yaw" errors due to inconsistent alignment of the image capturing device 40 and light source 10 with respect to the subject's eye 30. This can result in inconsistencies between the images used to generate the signature code table and those used to measure unknown concentrations.

As shown in step 490, the procedure is repeated by obtaining predetermined images that correspond to each of a desired number of known concentrations, and a concentration signature code table is generated as described previously.

Preferably, the diameter of the pupil of the subject's eye 30 is maintained at a constant value for each successive predetermined image and known glucose concentration to reduce variations in scenery characteristics of the iris caused by variations in pupil diameter.

Calculation of Unknown Glucose Values

Figure 14:
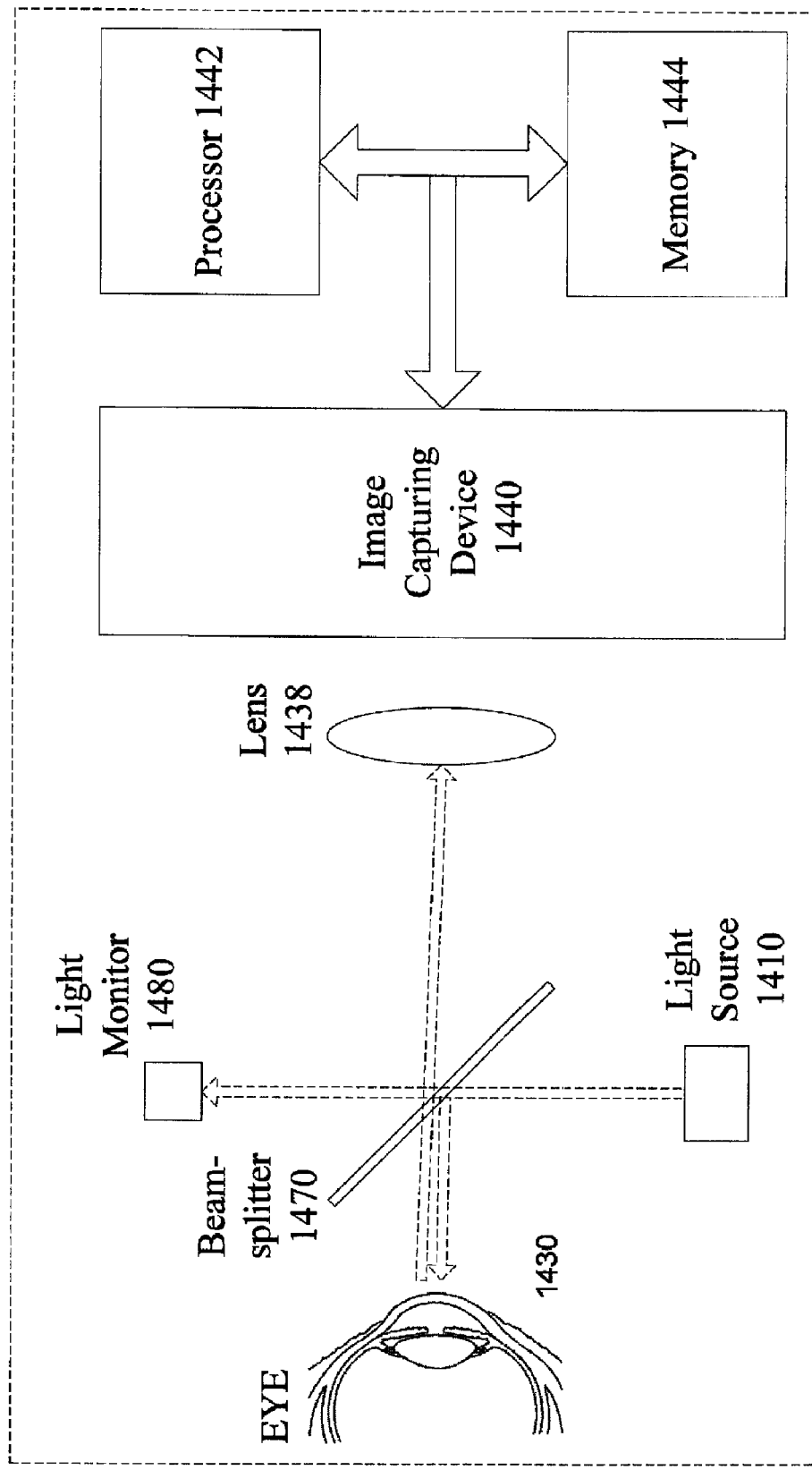
FIG. 14 is a depiction of an alternate system for measuring the concentrations of a substance.

Once the signature code table has been obtained, unknown concentration values can be determined using the system of FIG. 2 or alternatively, FIG. 14. Prior to capturing a measured image of the eye 30, the subject's pupil is preferably adjusted to match its diameter at the time the predetermined images were captured in connection with generating the signature code table.

Figure 5:
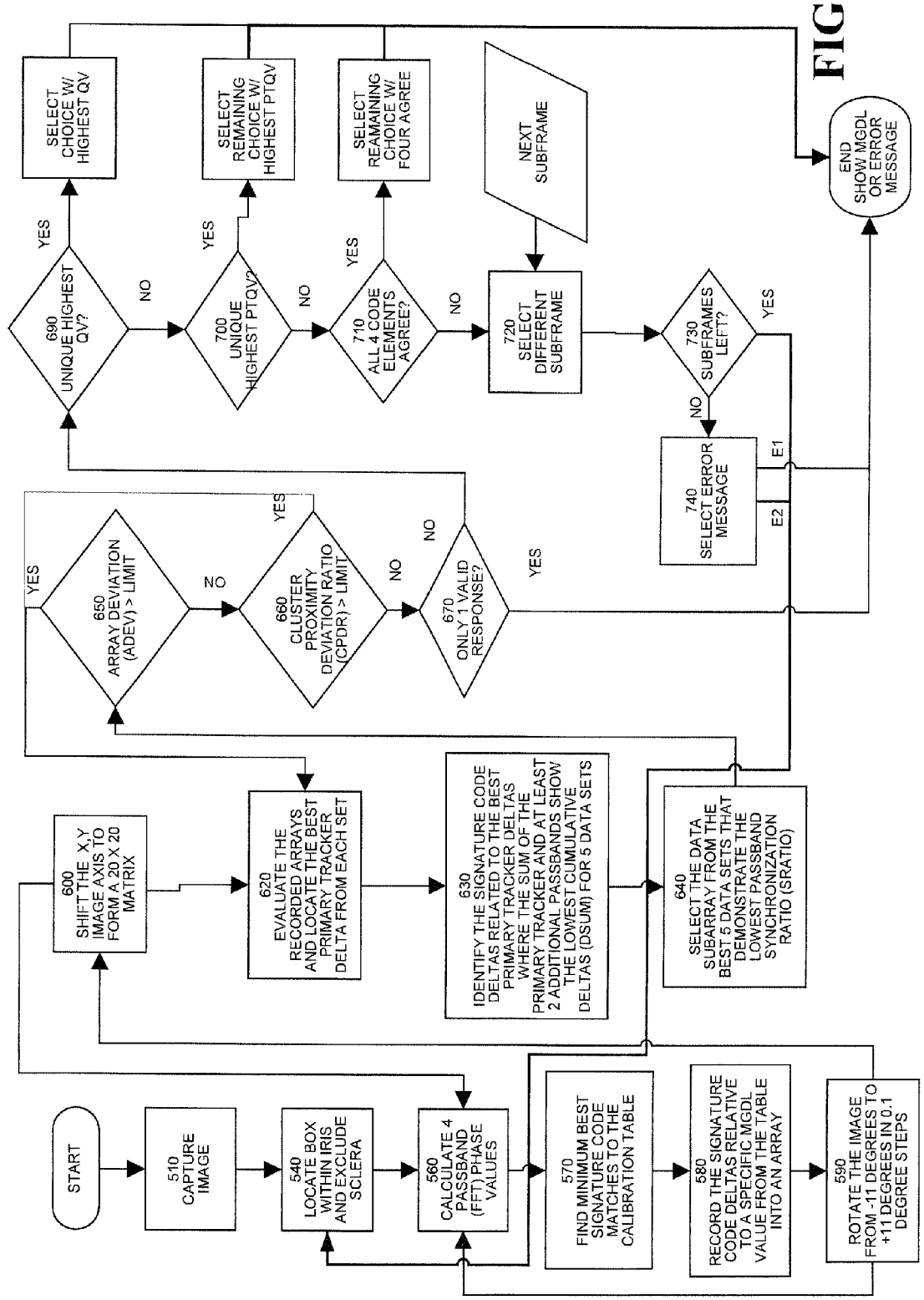
FIG. 5 is a flow chart depicting a method for measuring the concentration of an optically-active substance performed in one exemplary fashion.
Figure 6:
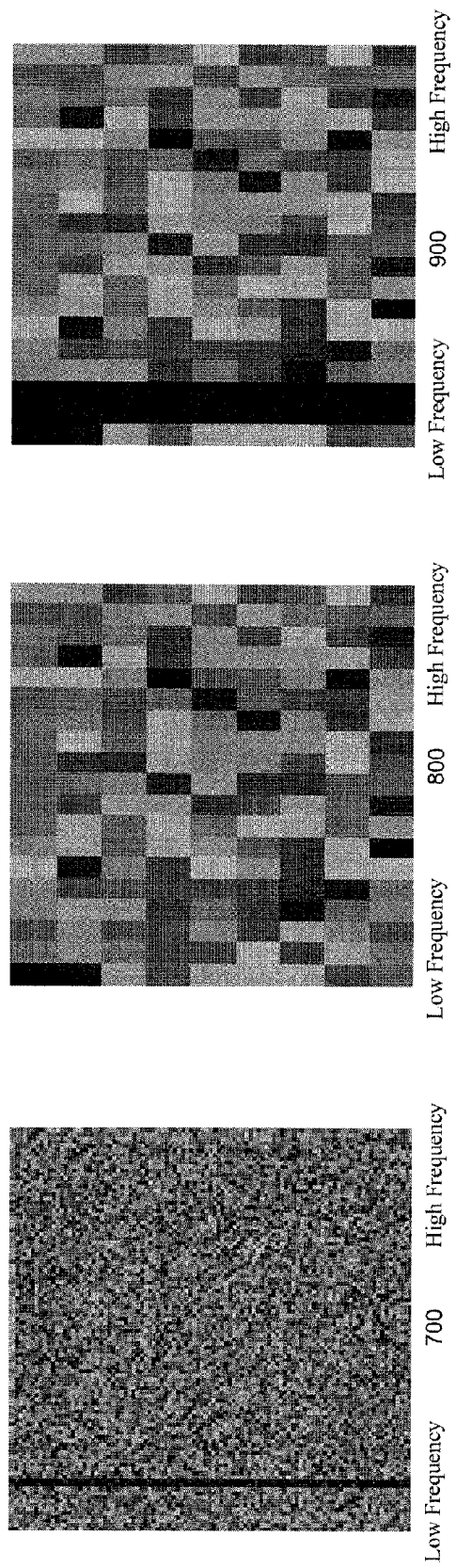
FIG. 6 illustrates a comparison of the FFT phase images that are shown in FIGS. 7-9.

FIG. 5 is a flow chart depicting a method for measuring the concentration of a chemical substance in accordance with a preferred embodiment of the present invention. According to the method, a measured image such as the one depicted in FIG. 3 is obtained in step 510 in the same way that predetermined images were obtained to generate the pattern-match table. A data set represented by box 80 is selected to include iris image 70 but exclude sclera image 60.

In step 540, Region of Interest (ROI) 150 and/or ROI 160 are used to extract spatial phase information such that the data corresponds to with the signature codes that were used to generate the predetermined signature code tables.

From the measured image, in step 540 all of the pixels in ROI boxes 150 and 160 are use to construct ROI subarrays to be used for processing of the image data. In step 560, the ROI information is used to produce two sets of four FFT phase tuned passbands.

In steps 570 and 580, The four element phase data are compared with each entry in the signature code calibration table (FIG. 15). The minimum phase value deltas and the associated concentration values (MgDI) index are recorded into an array.

In step 590, Steps 560-580 are repeated as the image is rotated through each ROI. The image rotation steps from −11 degrees to 11 degrees using 0.1 degree steps. A large area of the image is recorded as trail phase data sets to allow the hub search to take place.

Figure 16:
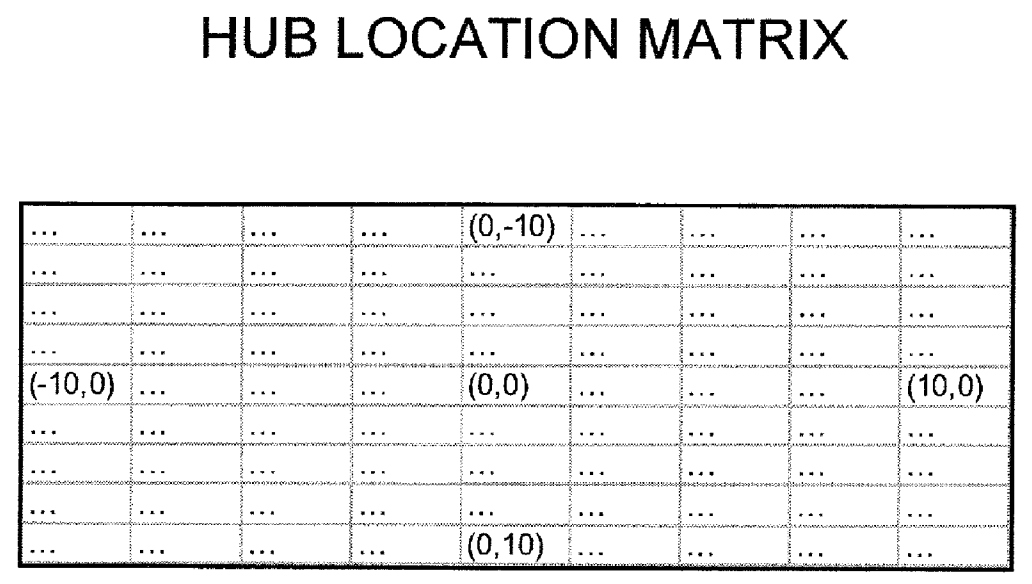

Step 600 repeats step 590 while horizontally and vertically slewing the complete input image as describe in step 510. Arrays are constructed from the comparison trial data that was recorded in step 590. Both the X and Y axis of the input image are stepped one pixel at a time from −10 steps to 10 steps to create a grid square matrix (FIG. 16). This process is used to locate the image orientation that produces a precise rotary hub lock (FIG. 12). The phase delta values that were recorded in step 600 are used to locate the common radius position for image areas that are scanned through each ROI for evaluation.

Step 620 evaluates the data that was created by step 600. The complete rotary scan subarrays are evaluated to identify the Best Delta Sum (BDSUM) statistic within each subarray. These arrays will be evaluated for probable hub locks.

Step 630 uses the data acquired in step 620 to identify which of five best match candidates demonstrate that the primary tracker and at least two additional passband phase deltas agree on a specific concentration value. The Delta Sum (DSUM) statistic is used to find the candidate with the lowest cumulative delta between phase values and the calibration table signature code table. The DSUM value is comprised of the best phase delta values from equal or adjacent concentration phase entries in the calibration table. The table index positions (FIG. 15) are evaluated so that if, for example, the MgDI value that associates with index=2 has DSUM components that locate positions 1 and 3 a match is determined. The average of the three MgDI values becomes the estimated answer. This methodology forms the basis for interpolation between known concentration values in the table.

Step 640 evaluates the five subarrays that were chosen with step 630. The rotational locations for each of the best phase deltas that comprised the DSUM values are checked for positional synchronization. The positional spread between the extreme phase match positions is the Synchronization Ratio (SRATIO). The candidate from the best five that was selected in step 630 that has the lowest SRATIO number is selected. A concentration is identified that associates with the best signature code agreement and the best spatial position concurrence with the image.

Step 650 computes the Array Deviation (ADEV) statistic for the best choice that was made in step 640. The step-to-step rotary comparisons that were performed during the BDSUM search in step 620 produces the data for this evaluation. A pre-set threshold is used to determine if the rotary scan array for an estimated concentration is rational. Hub centering errors and visual scenery artifacts such as eyelids and eyelashes in the image upset the global tracking continuity and invalidate the measurement. If the error threshold is exceeded processes 620-640 are repeated while removing the current estimation candidate from the list of best five.

Step 660 examines the Cluster Proximity Deviation Ratio (CPDR) for similar delta magnitudes between the signature component phase deltas. A cluster of the best three components within a signature code match is evaluated for the lowest spread ratio between the elements. A sanity threshold is used to ascertain if the variation of the matching phase delta elements are reasonable. A ratio of less than 2:1 is needed to pass the test. If the threshold is violated steps 620-650 are repeated.

Step 670 determines that if only one of the five candidates remains valid after step 660 it is declared the best answer for the ROI box under analysis. It is ready to compare with the final result obtained from the alternate ROI analysis. If more than one of the five choices remain valid the process moves to step 690.

Step 690 examines the remaining candidates from the list of five for one with the highest Q value. This response is determined by the number of times the same answer was selected during the rotary scan. Excellent hub alignment and a very consistent global correlation are implied. If the highest QV is associated with the best candidate (lowest BDSUM) from step 670 it is chosen as the answer.

Step 700 examines the remaining candidates from the list of five for one with the highest Primary Tracker Q value (PTQV). Rotary position concurrence of a selection implies excellent Primary Tracking agreement. If the highest PTQV is associated with the best candidate (lowest BDSUM) from step 670 it is chosen as the answer.

Step 710 examines the remaining candidates from the list of five for one with the highest concurrence of signature code elements. A minimum of a three element agreement is needed to get beyond step 670. In steps 690-700 cannot resolve the answer the candidates are examined to see if all four signature code elements AGREE with a specific glucose estimation. If so, that choice with the four code agreement is used as the answer.

Step 720 is reached only if none of the candidates are selected as a good answer. A new subframe image is selected to allow the entire process to be repeated from step 560.

Step 730 determines if additional subframes are available for processing because the current subframe image did not produce a valid answer. This response will require the user to re-mount the camera and take another measurement. Steps 510-720 are repeated. If a valid answer was not found after processing all of the available subframes the process continues to step 740.

Step 740 causes an error message to be displayed to the user and terminates the process in one embodiment (E1). In another embodiment (E2) repetition of the entire sequence from step 560 processes the alternate ROI. If a valid answer cannot be found from either ROI the error message is displayed and the process is terminated.

FIG. 14 is an alternate embodiment of an image capture system where a light source 1410 projects light toward an eye 1430 through a beam-splitter 1470. Light monitor 1480 is a photo-detector that can be used to measure the intensity of light source 1410. This image capture system prevents the light source 1410 from partially obstructing the ability of an image capture device 1440 from capturing an image of the eye 1430 through a lens 1438.

As depicted in FIG. 14, image capturing device 1440 is optionally connected to a processor 1442, which is configured to calculate a glucose concentration, as described above.

What is claimed is:

1. A method of determining the concentration of a chemical substance that produces refractive and/or polarization changes when light is passed through the aqueous fluids in the eye, the method comprising:
   measuring a spatial position change within an image of an eye comprising a corneal surface illumination gradient reference portion and an internal eye illumination gradient image portion while maintaining a predetermined degree of precision due to the mathematically consistent spatial ratio between the reference and the measured illumination intensity gradients across the surface of both images in the presence of focus and imager alignment errors;
   utilizing a surface of the cornea as an illumination gradient reference image; and
   determining the change within the internal eye illumination gradient image using the reference image, wherein a difference between a spatially shifted illumination gradient across the internal eye image portion and an unshifted illumination gradient across the returned corneal surface image portion is a mechanically stable ratio that enables the precise measurement of all spatial positional shifts of the internal eye illumination gradient image.

* * * * *